(12) United States Patent
Yanagawa et al.

(10) Patent No.: US 6,462,231 B1
(45) Date of Patent: Oct. 8, 2002

(54) METHOD OF PRODUCING CARBOXYLIC ACID AND ALCOHOL

(75) Inventors: Masatoshi Yanagawa, Niigata-ken (JP); Kazunori Watanabe, Okayama-ken (JP); Fumio Nakahara, Okayama-ken (JP)

(73) Assignee: Kuraray Co., Ltd., Kurashiki (JP)

( * ) Notice: Subject to any disclaimer, the term of this patent is extended or adjusted under 35 U.S.C. 154(b) by 0 days.

(21) Appl. No.: 09/594,767

(22) Filed: Jun. 16, 2000

(30) Foreign Application Priority Data

Jun. 16, 1999 (JP) .......................................... 11-169331

(51) Int. Cl.[7] .......................... C07C 53/00; C07C 53/08
(52) U.S. Cl. ........................ 562/512; 562/607; 562/608
(58) Field of Search ................................ 562/512, 607, 562/608; 203/83, 85

(56) References Cited

U.S. PATENT DOCUMENTS

| | | | |
|---|---|---|---|
| 2,936,321 A | 5/1960 | Mercier ...................... | 260/541 |
| 4,352,940 A | * 10/1982 | Adelman et al. ........... | 562/607 |
| 5,770,770 A | 6/1998 | Kim et al. ................... | 562/608 |

FOREIGN PATENT DOCUMENTS

GB 687902 2/1953

OTHER PUBLICATIONS

Yoshio Fuchigami, "Hydrolysis of Methyl Acetate in Distillation Column Packed With Reactive Packing of Ion Exchange Resin", J. Chem. Eng. Jpn., vol. 23 (1990), pp. 354–358.*

S.J. Han et al, "Application of a Fluidized Reation–Distillation Column for Hydrolysis of Methyl Acetate", Chem. Eng. J., vol. 66 (1997), pp. 227–230.*

* cited by examiner

Primary Examiner—Sreeni Padmanabhan
Assistant Examiner—Farhad Forohar
(74) Attorney, Agent, or Firm—Oblon, Spivak, McClelland, Maier & Neustadt, P.C.

(57) ABSTRACT

A method of producing carboxylic acid and alcohol, that includes: supplying a liquid to a first distillation tower, said liquid including a carboxylic acid ester, and said first distillation tower being operated in a total reflux condition, to obtain a side stream; supplying said side stream to a hydrolysis reactor that includes an acid catalyst to obtain a reaction product liquid that includes a carboxylic acid, an alcohol, water and a carboxylic acid ester; supplying said reaction product liquid to said first distillation tower and removing a first bottom liquid therefrom, said first bottom liquid including a carboxylic acid, an alcohol and water; supplying said first bottom liquid to a second distillation tower and separating said first bottom liquid into a first top distillate that includes an alcohol, and a second bottom liquid that includes a carboxylic acid and water; supplying said second bottom liquid to a third distillation tower and separating said second bottom liquid into a second top distillate that includes a carboxylic acid and water, and a third bottom liquid that includes a carboxylic acid; circulating said second top distillate back to a tower top of said first distillation tower, and adding water to said tower top.

19 Claims, 2 Drawing Sheets

METHOD OF PRODUCING CARBOXYLIC ACID AND ALCOHOL

BACKGROUND OF THE INVENTION

1. Field of the Invention

The present invention concerns a method of producing carboxylic acid and alcohol. More specifically, this invention concerns a method of producing carboxylic acid and alcohol by hydrolysis of a liquid, which contains a carboxylic acid ester, under the presence of an acid catalyst to obtain a reaction product liquid, comprised essentially of carboxylic acid, alcohol, water, and carboxylic acid ester, and distilling this reaction product liquid in a manner that is industrially advantageous.

2. Description of the Related Art

For the conventional production of polyvinyl alcohol, vinyl acetate is obtained by an acetoxylation reaction, in which ethylene and acetic acid are the raw materials; polymerizing this vinyl acetate to produce vinyl polyacetate; and performing an ester exchange reaction with methanol in the presence of a basic catalyst. The methyl acetate that is produced from the ester exchange reaction is hydrolyzed in the presence of an acid catalyst and recovered in the final stage as acetic acid and methanol, and the unreacted methyl acetate is circulated back and reused in the hydrolysis reaction.

A method of recovering methyl acetate as acetic acid and methanol is disclosed in p. 109 of "Poval, " edited by the Polymer Society of Japan (newly revised edition; Apr. 1, 1981). This method shall now be described with reference to FIG. 3. A saponification mother liquor, having methyl acetate and methanol as the principal components, is supplied from a saponification mother liquor feeding line 17 to an A distillation tower 18 and separated into a top distillate 19, having methylacetate and methanol as the principal component, and a bottom liquid 20, having methanol as the principal component. The top distillate 19 is fed into an extractive distillation tower 21 along with the return distillate from the top distillate 27 of a B distillation tower 26 (described below), and water is added to the tower top of extractive distillation tower 21 from extraction water feeding line 22 to perform extractive distillation.

Figure 3:
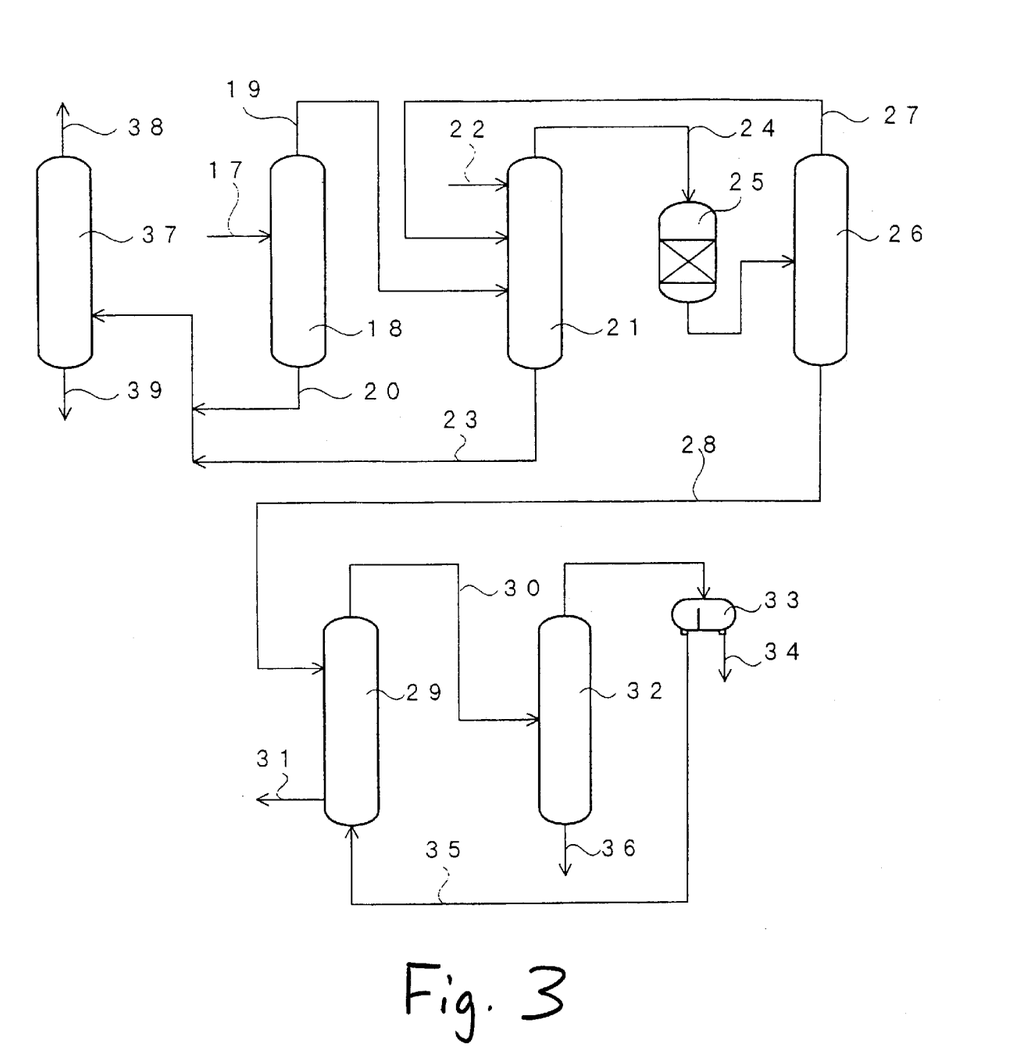
FIG. 3 is a schematic flow diagram of an embodiment of a conventional method.

The bottom liquid 23 of extractive distillation tower 21 has methanol as the principal component and is fed along with the abovementioned bottom liquid of A distillation tower 18 to a C distillation tower 37 and separated into a methanol distillate 38 and a bottom liquid 39, which contains sodium acetate, etc. Methanol distillate 38 is treated further as necessary and recovered as methanol. The top distillate of extractive distillation tower 21 is methyl acetate and water and is supplied from methyl acetate feeding line 24 to a hydrolysis reactor 25, filled with ion exchange resin or other acid catalyst, to obtain a reaction product liquid, which essentially contains acetic acid, methanol, water, and unreacted methyl acetate. This reaction product liquid is fed into B distillation tower 26 and separated into a top distillate 27, which contains methyl acetate and methanol, and a bottom liquid 28, which contains acetic acid and water. The top distillate 27 is the abovementioned return distillate, and this distillate is fed into extractive distillation tower 21. Hereinafter, the components of the mixture shall refer mainly to the principal components, and descriptions concerning minor components present only in small amounts may be omitted. The Figures are conceptual diagrams, and the reboiler, condenser, pump, and other accessory equipment that are normally used are all unillustrated.

The bottom liquid 28, which contains acetic acid and water, of B distillation tower 26 is fed to the tower top of extraction tower 29 and acetic acid esters, ketones, and other solvents are fed from the lower part of the extraction tower to extract acetic acid. 35 is the solvent feeding line, and 31 is the rundown line for the raffinate, which has water as the principal component. The extracted liquid 30 from the extraction tower top includes acetic acid, solvent, and water, and this extracted liquid is fed into azeotropic distillation tower 32, having the abovementioned solvents as the azeotrope former, and acetic acid is recovered from the lower part of this distillation tower. 36 is a recovery line for acetic acid. The top distillate of azeotropic distillation tower 32 is water and solvent, and this top distillate is separated by separator 33, and the solvents are circulated back from the abovementioned solvent feeding line 35 for use in the extraction tower, and the water is taken out via drain line 34.

However, the above-described conventional method has the following problems. Since the equilibrium constant of the hydrolysis reaction of methylacetate and water is small, being 0.14 at 50° C. for example, and the temperature dependence thereof is also small. Thus when the hydrolysis reaction is carried out with a molar ratio of methyl acetate to water of 1, the degree of conversion of methyl acetate by hydrolysis will only be 27 mole % at the most. Since, as mentioned above, the temperature dependence of the equilibrium constant is very small, substantially improving the degree of conversion by hydrolysis is not possible even if the reaction temperature is increased. Although the degree of conversion by hydrolysis can be improved by increasing the molar ratio of water to methyl acetate, the acetic acid concentration of the bottom liquid of B distillation tower 26 will drop and the load placed on extraction tower 29 for concentrating the acetic acid will increase.

Thus, with the conventional method, an extraction tower is required for the acetic acid concentration process. In addition, not only is the load on the extraction tower increased when the molar ratio of water to methyl acetate is increased, but the azeotropic distillation tower 32 must also be operated with caution in order to prevent solvents and water from becoming mixed with acetic acid. An extremely large amount of labor is thus required for the operation of the conventional method. Although the above description relates to an example where methyl acetate is hydrolyzed, the same applies to other carboxylic acid esters.

A reactive distillation method to recover methyl acetate as acetic acid and methanol is disclosed in U.S. Pat. No. 5,770,770. With this method, hydrolysis is performed without taking methyl acetate out of the system, and the generated components can be separated by distillation at the same time. This method can thus be said to be a rational method. However, in order to increase the degree of conversion by hydrolysis by this method, the molar ratio of water must be large with respect to methyl acetate, and since the amount of energy required to produce acetic acid and methanol therefore becomes significantly large, the method is not industrially advantageous.

SUMMARY OF THE INVENTION

An object of the present invention is therefore to provide a method of producing alcohol and carboxylic acid from a carboxylic acid ester in an industrially advantageous manner by a simplified process that does not use solvents.

This and other objects have been achieved by the present invention, the first embodiment of which provides a method of producing carboxylic acid and alcohol, that includes:

hydrolysing a liquid in a hydrolysis reactor, said hydrolysis reactor including an acid catalyst, and said liquid including: (1) a carboxylic acid ester; and (2) at least a portion of a side stream taken from a first distillation tower operated in a total reflux condition, to obtain a reaction product liquid that includes a carboxylic acid, an alcohol, water and a carboxylic acid ester;

supplying said reaction product liquid to said first distillation tower and removing a first bottom liquid therefrom, said first bottom liquid including a carboxylic acid, an alcohol and water;

supplying said first bottom liquid to a second distillation tower and separating said first bottom liquid into a first top distillate that includes an alcohol, and a second bottom liquid that includes a carboxylic acid and water;

supplying said second bottom liquid to a third distillation tower and separating said second bottom liquid into a second top distillate that includes a carboxylic acid and water, and a third bottom liquid that includes a carboxylic acid;

circulating said second top distillate back to a tower top of said first distillation tower, and adding water to said tower top.

Another embodiment of the invention provides a method of producing carboxylic acid and alcohol, that includes:

supplying a liquid to a first distillation tower, said liquid including a carboxylic acid ester, and said first distillation tower being operated in a total reflux condition, to obtain a side stream;

supplying said side stream to a hydrolysis reactor that includes an acid catalyst to obtain a reaction product liquid that includes a carboxylic acid, an alcohol, water and a carboxylic acid ester;

supplying said reaction product liquid to said first distillation tower and removing a first bottom liquid therefrom, said first bottom liquid including a carboxylic acid, an alcohol and water;

supplying said first bottom liquid to a second distillation tower and separating said first bottom liquid into a first top distillate that includes an alcohol, and a second bottom liquid that includes a carboxylic acid and water;

supplying said second bottom liquid to a third distillation tower and separating said second bottom liquid into a second top distillate that includes a carboxylic acid and water, and a third bottom liquid that includes a carboxylic acid;

circulating said second top distillate back to a tower top of said first distillation tower, and adding water to said tower top.

With the present invention, since the reaction product liquid obtained by the hydrolysis reaction is fed into a first distillation tower, this distillation tower is operated in a total reflux condition. Accordingly, the carboxylic acid ester is not distilled-outside the system but rather is taken from the distillation tower as a side stream and fed to the hydrolysis reactor. The water of the amount consumed by hydrolysis is added to the tower top of the distillation tower to perform extractive distillation by water, and the concentration of the aqueous solution of carboxylic acid is not performed by the azeotropic distillation method. Carboxylic acid and alcohol can thus be produced in a stable manner from a carboxylic acid ester with an extremely simplified flow. In addition, with the present invention, since the amount of water used can be significantly reduced, the amount of waste water is significantly reduced.

DETAILED DESCRIPTION OF THE PREFERRED EMBODIMENTS

A more complete appreciation of the invention and many of the attendant advantages thereof will be readily obtained as the same becomes better understood by reference to the following description when considered in connection with the accompanying drawings, in which like reference characters designate like or corresponding parts throughout the several views and wherein:

Preferably, in the first embodiment of the invention, a liquid, which contains the carboxylic acid ester and with which at least a part of the components thereof is a side stream taken out from a first distillation tower operated in the total reflux condition, is supplied to a hydrolysis reactor filled with acid catalyst to obtain a reaction product liquid comprised essentially of carboxylic acid, alcohol, water, and carboxylic acid ester; the above-mentioned reaction product liquid is supplied to the abovementioned first distillation tower, and a bottom liquid, comprised essentially of carboxylic acid, alcohol, and water, is taken out from the bottom of the abovementioned distillation tower; the abovementioned bottom liquid is separated in a second distillation tower into a top distillate, having alcohol as the principal component, and a bottom liquid, comprised of carboxylic acid and water; the abovementioned bottom liquid is separated in a third distillation tower into a top distillate, comprised of carboxylic acid and water, and a bottom liquid, comprised of carboxylic acid; the abovementioned top distillate is circulated back to the tower top of the abovementioned first distillation tower; and water is added to the abovementioned tower top.

Preferably, in the second embodiment of the invention, a liquid, which contains the carboxylic acid ester, is supplied to a first distillation tower that is operated in the total reflux condition, the side stream taken out from the abovementioned distillation tower is supplied to a hydrolysis reactor filled with acid catalyst to obtain a reaction product liquid comprised essentially of carboxylic acid, alcohol, water, and carboxylic acid ester; the abovementioned reaction product liquid is supplied to the abovementioned first distillation tower; a bottom liquid, comprised essentially of carboxylic acid, alcohol, and water, is taken out from the bottom of the abovementioned distillation tower; the abovementioned bottom liquid is separated in a second distillation tower into a top distillate, having alcohol as. the principal component, and a bottom liquid, comprised of carboxylic acid and water; the abovementioned bottom liquid is separated in a third distillation tower in to a top distillate, comprised of carboxylic acid and water, and a bottom liquid, comprised of carboxylic acid; the abovementioned top distillate is circulated back to the tower top of the abovementioned first distillation tower; and water is added to the abovementioned tower top.

Figure 1:
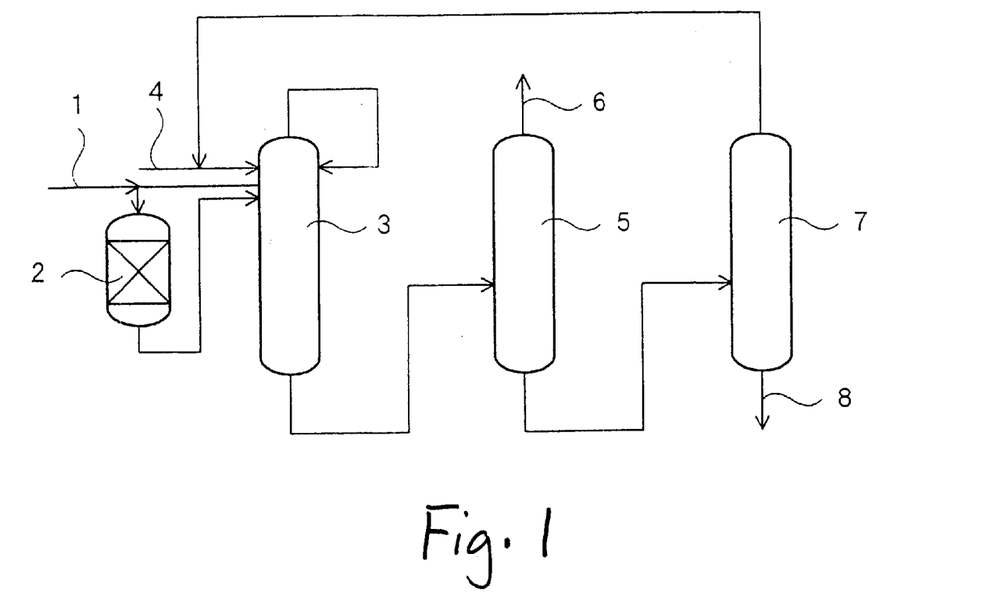
FIG. 1 is a schematic flow diagram of an embodiment of this invention.

FIG. 1 is a flowchart that illustrates a preferred method of producing alcohol and carboxylic acid from a liquid that contains a carboxylic acid ester according to one embodiment of the invention. The carboxylic-acid-ester-containing liquid, which is the raw material, is fed from carboxylic acid ester feeding line 1 to a hydrolysis reactor 2, filled with an acid catalyst, and is hydrolyzed in the liquid phase to obtain a reaction product liquid comprised essentially of carboxylic acid, alcohol, water and unreacted carboxylic acid ester. The abovementioned liquid that contains the carboxylic acid ester also contains the side stream from a first distillation tower, to be described below, as at least part of the components thereof. The carboxylic-acid-ester-containing liquid that is fed into the hydrolysis reactor is thus comprised of a carboxylic-acid-ester-containing liquid that is supplied from outside the system and a carboxylic acid-ester-containing liquid that is the side stream from the first distillation tower. Though the ratio of the amounts of the carboxylicacid-ester-containing liquid that is supplied from outside the system and the carboxylic-acidester-containing liquid that is the side stream from the first distillation tower will preferably depend on the number of stages of the first distillation tower that is used and cannot be set unconditionally, the ratio is most preferably set in the range, 1:5 to 10 (weight ratio). Though examples of the acid catalyst include mineral acids, such as sulfuric acid, and solid acid catalysts, the use of a solid acid catalyst is more preferable in that the trouble of separating and recovering a mineral acid in the liquid condition can be avoided. An ion exchange resin is an especially preferable example of a solid acid catalyst. If acetic acid or other acid is contained in the liquid, that acid may also function as the acid catalyst.

The above-mentioned reaction product liquid is supplied to the first distillation tower 3, which uses an aqueous solution of carboxylic acid as the solvent and is an extractive distillation tower that is operated in the total reflux condition, and is separated into a top distillate, comprised of carboxylic acid ester, alcohol, and water, and a bottom liquid, comprised of carboxylic acid, alcohol and water. Preferably, a plate tower having 25 to 60 stages and more preferably 30 to 40 stages, is used as the first distillation tower, and if the tower top is counted as the first stage, the abovementioned reaction product liquid is preferably fed to the second to tenth stage from the tower top of the first distillation tower. Since the ratio of water to carboxylic acid of the bottom liquid of the first distillation tower, which is comprised of carboxylic acid, alcohol, and water, will be disadvantageous thermally if it is too large and will be disadvantageous in terms of the hydrolysis reaction if it is too small, the ratio of water to carboxylic acid, as a weight ratio, is preferably in the range, 1:1 to 1:4.

The above-mentioned bottom liquid is separated into a top distillate, comprised of alcohol, and a bottom liquid, comprised of carboxylic acid and water, in a second distillation tower 5, which is preferably operated at a reflux ratio of 0.5 to 3. The alcohol, which is the top distillate, is recovered from alcohol recovery line 6. Preferably, a plate tower of 50 to 80 stages is used as the second distillation tower, and the bottom liquid of the first distillation tower is preferably fed near the middle stage of the second distillation tower. Though carboxylic acid and alcohol exist in the bottom liquid of the first distillation tower and the carboxylic acid may exhibit the functions of a catalyst as mentioned above so that a carboxylic acid ester is produced, since the carboxylic acid ester is distilled and separated in the first distillation tower and supplied to the hydrolysis reactor, it will be recovered in the final stage as carboxylic acid and alcohol and will not present any problems in particular.

The bottom liquid of second distillation tower 5 is preferably an aqueous solution of carboxylic acid of a concentration of approximately 20 to 50 wt %. This aqueous solution is fed into a third distillation tower 7 and is separated into a top distillater comprised of an aqueous solution of carboxylic acid, and a bottom liquid, comprised of carboxylic acid, at a preferred reflux ratio of 1 to 3. The top distillate is circulated back to the tower top of the abovementioned first distillation tower 3 and is used along with the extraction water fed from extraction wafer feeding line 4 as the solvent of first distillation tower 3, which is an extractive distillation tower. The carboxylic acid is recovered from carboxylic acid recovery line 8. Preferably, a plate tower of approximately 60 to 70 stages is used as the third distillation tower, and the bottom liquid of the second distillation tower is preferably fed to the 20th to 25th stage from the tower top. With regard to the carboxylic acid concentration of the aqueous solution of carboxylic acid, which is the distillate from tower top, a concentration that is too high will be disadvantageous for the hydrolysis reaction of the carboxylic acid ester and a concentration that is too low will be disadvantageous thermally. The carboxylic acid concentration is thus preferably 6 to 15 wt %. Though the bottom liquid of third distillation tower 7 may be used as it is as product acetic acid, it may be used upon being refined further as necessary or may be used upon being taken out as a side stream from the lower part of the distillation tower.

This invention is preferably characterized in that the solvent in the first distillation tower 3 is used in the hydrolysis reaction. In the first aspect of this invention, the reaction product liquid obtained by the hydrolysis reaction is fed into the first distillation tower, this distillation tower is operated in the total reflux condition so that the carboxylic acid ester is not distilled out of the system but is taken out as a side stream and fed to the hydrolysis reactor and water of the amount consumed by hydrolysis is added to the tower top of the distillation tower to perform extractive distillation by water. The stage at which the side stream is taken out from the first distillation tower is preferably the same as the stage at which the hydrolysis reaction product liquid is fed or is a stage, which is below the tower top and is one to three stages above the abovementioned feeding stage. By this method, not only can carboxylic acid and alcohol be produced in a thermally advantageous manner from a carboxylic acid ester but since the waste water can be reduced significantly, the method provides advantages in terms of the environment as well.

As has been described above, with the present invention, the top distillate of third distillation tower 7, which is comprised of an aqueous solution of carboxylic acid, is circulated back and used as the solvent for the abovementioned extractive distillation. The hydrolysis reaction of the carboxylic acid ester is thus performed under the presence of the carboxylic acid. Examinations by the present inventors have shown that though the presence of carboxylic acid, which is part of the product system, in the hydrolysis reaction of the carboxylic acid ester will be somewhat disadvantageous for the hydrolysis reaction of the carboxylic acid ester, the influence is not very large, and in view that the distillation for obtaining the above-mentioned aqueous solution of carboxylic acid may be of the level of crude distillation and will thus be easy in operation and in view of the thermal effects, the presence of carboxylic acid in the hydrolysis reaction of the carboxylic acid ester is not disadvantageous at all as a whole.

Figure 2:
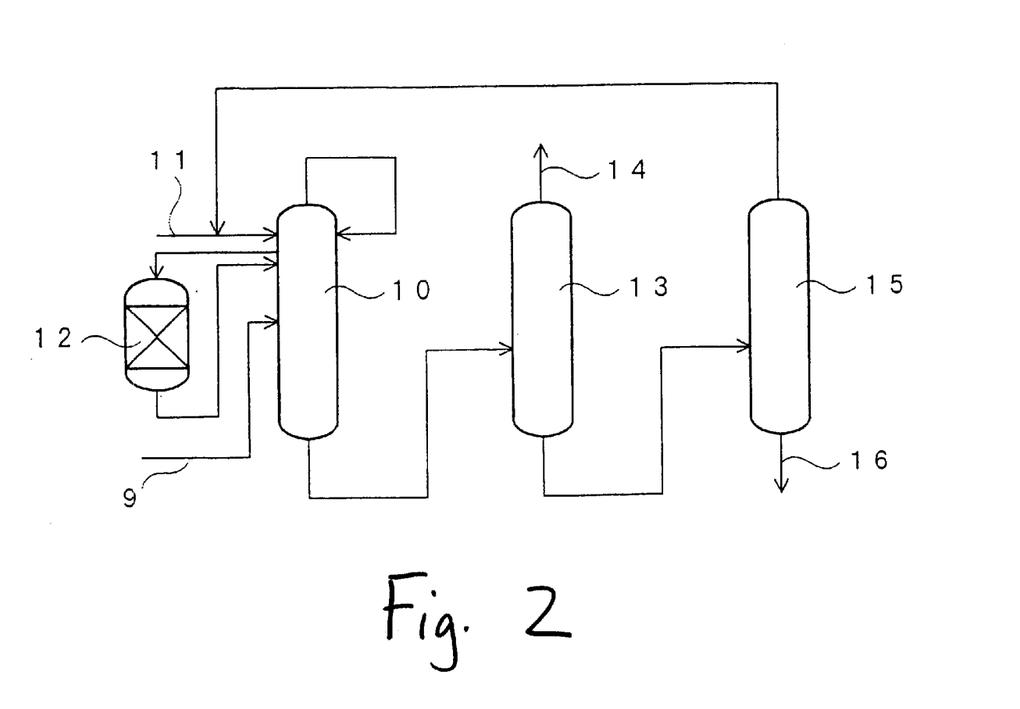
FIG. 2 is a schematic flow diagram of another embodiment of this invention.

FIG. 2 is a flowchart that shows another preferred embodiment of this invention for producing alcohol and carboxylic acid from a liquid, which contains a carboxylic acid ester. The carboxylic-acid-ester-containing liquid, which is the raw material, is fed from carboxylic acid ester feeding line 9 into a first distillation tower 10, which uses an aqueous solution of carboxylic acid as the solvent and is operated in the total reflux condition, and is separated into a top distillate, comprised of carboxylic acid ester and alcohol, and a bottom liquid, comprised of carboxylic acid, alcohol and water. Preferably, a plate tower of approximately 30 to 70 stages is used as first distillation tower 10 and the carboxylic-acid-ester-containing liquid is preferably fed near the middle stage of the first distillation tower. The bottom liquid of the first distillation tower is separated into a top distillate, comprised of alcohol, and a bottom liquid, comprised of carboxylic acid and water, in a second distillation tower 13, and the alcohol, which is the top distillate, is recovered from alcohol recovery line 14. Second distillation tower 13 is the same as second distillation tower 5 described with reference to FIG. 1 and the operation conditions are the same as well.

The bottom liquid of second distillation tower 13 is preferably an aqueous solution of carboxylic acid of a concentration of approximately 20 to 50 wt %. This aqueous solution is fed into a third distillation tower 15 and is separated into a top distillater comprised of an aqueous solution of carboxylic acid, and a bottom liquid, comprised of carboxylic acid, and the top distillate is circulated back to the tower top of the abovementioned first distillation tower 10 and is used as the solvent of first distillation tower 10. The carboxylic acid is recovered from carboxylic acid recovery line 16. Third distillation tower 15 is the same as third distillation tower 7 described with reference to FIG. 1 and the operation conditions are the same as well. With regard to the carboxylic acid concentration of the aqueous solution of carboxylic acid, which is the distillate from tower top, a concentration that is too high will be disadvantageous for the hydrolysis reaction of the carboxylic acid ester and a concentration that is too low will be disadvantageous thermally. The carboxylic acid concentration is thus preferably 6 to 15 wt %. The top distillate of third distillation tower 15, which is comprised of en aqueous solution of carboxylic acid, is circulated back to the abovementioned first distillation tower 10 and used along with the extraction water supplied from extraction water feeding line 11 as the solvent of first distillation tower 10, which is an extractive distillation tower.

As has been mentioned above, this invention is characterized in that the solvent in the first distillation tower is used for the hydrolysis reaction. With the method of this invention illustrated in FIG. 2, the side stream taken out from first distillation tower 10 is fed into the abovementioned hydrolysis reactor 12, which is filled with an acid catalyst. and the reaction product liquid obtained by hydrolysis is fed into first distillation tower 10. The stage at which the side stream is to be taken out from the first distillation tower is preferably the same stage as that into which the hydrolysis reaction product liquid is fed or a stage that is below the tower top and one to three stages above the aforementioned feeding stage. Since the amount of extraction water used in first distillation tower 10 can be reduced significantly with this method as well, the amount of waste water can be lessened. As in the description given with reference to FIG. 1, the ratio of water to carboxylic acid of the bottom liquid of the abovementioned distillation tower, which is comprised of carboxylic acid, alcohol, and water, is preferably set to a weight ratio of 1:1 to 1:4.

Preferable examples of the carboxylic acid include propionic acid, acetic acid, butyric acid, valeric acid, caproic acid, lactic acid, etc. Preferable examples of the alcohol include methanol, ethanol, propanol, butanol, etc. A lower alcohol is preferable in terms of dissolution properties, boiling point, azeotropic properties, etc. Preferable examples of carboxylic acid esters include carboxylic acid esters of the above compoumds. From the standpoint of industrial usefulness, acetic acid is more preferable as the carboxylic acid, and methyl acetate or ethyl acetate are more preferable as the carboxylic acid ester. Most preferable examples of methyl acetate and ethyl acetate include methyl acetate, which has been produced by the ester exchange reaction of polyvinyl acetate and methanol under the presence of a basic catalyst, methyl acetate or ethyl acetate, which has been produced by the reaction of (x-acetoxy- or propionoxy-propionic acid and methanol or ethanol under the presence of an acid catalyst, etc.

The carboxylic acid ester, which is the raw material, may contain an alcohol or carboxylic acid, which is higher in boiling point than the carboxylic acid ester and, if the alcohol or carboxylic acid forms an azeotrope with the carboxylic acid ester, can be extracted with water. A method illustrated in FIG. 1 or FIG. 2 can be selected suitably according to the content of such an alcohol or carboxylic acid. Normally, it is preferable in terms of putting this invention into practice in an industrially advantageous manner to employ the method of FIG. 1 when the content of such components is less than 20 wt %, and to employ the method of FIG. 2 when the content is equal to or greater than 20 wt %.

An especially preferable embodiment, A, is a method of producing carboxylic acid and alcohol by obtaining a reaction product liquid by hydrolysis of a carboxylic acid ester under the presence of an acid catalyst and separating said product liquid by distillation, said method of producing carboxylic acid and alcohol being characterized in that a liquid, which contains the carboxylic acid ester and with which at least a part of the components thereof is a side stream taken out from a first distillation tower operated in the total reflux condition, is supplied to a hydrolysis reactor filled with acid catalyst to obtain a reaction product liquid comprised essentially of carboxylic acid, alcohol, water, and carboxylic acid ester, said reaction product liquid is supplied to said first distillation tower, a bottom liquid, comprised essentially of carboxylic acid, alcohol, and water, is taken out from the bottom of said distillation tower, said bottom liquid is separated in a second distillation tower into a top distillate, having alcohol as the principal component, and a bottom liquid, comprised of carboxylic acid and water. said bottom liquid is separated in a third distillation tower into a top distillate, comprised of carboxylic acid and water, and a bottom liquid, comprised of carboxylic acid, said top distillate is circulated back to the tower top of said first distillation tower, and water is added to said tower top.

Another especially preferable embodiment, B, is a method of producing carboxylic acid and alcohol by obtaining a reaction product liquid by hydrolysis of a carboxylic acid ester under the presence of an acid catalyst and separating said product liquid by distillation, said method of producing carboxylic acid and alcohol being characterized in that a liquid, which contains the carboxylic acid ester, is supplied to a first distillation tower that is operated in the total reflux condition, the side stream taken out from said distillation tower is supplied to a hydrolysis reactor filled with acid catalyst to obtain a reaction product liquid comprised essentially of carboxylic acid, alcohol, water, and carboxylic acid ester, said reaction product liquid is supplied to said first distillation tower, a bottom liquid, comprised essentially of carboxylic acid, alcohol, and water, is taken out from the bottom of said distillation tower, said bottom liquid is separated in a second distillation tower into a top distillate, having alcohol as the principal component, and a bottom liquid, comprised of carboxylic acid and water, said bottom liquid is separated in a third distillation tower into a top distillate, comprised of carboxylic acid and water, and a bottom liquid, comprised of carboxylic acid, said top distillate is circulated back to the tower top of said first distillation tower, and water is added to said tower top.

Another especially preferable embodiment is a method of producing carboxylic acid and alcohol as set forth in the above-mentioned embodiments A and/or B, wherein the acetic acid ester is methylacetate.

Another especially preferable embodiment is a method of producing carboxylic acid and alcohol as set forth in the above-mentioned A and/or B, wherein the acetic acid ester is ethyl acetate.

Another especially preferable embodiment is a method of obtaining carboxylic acid and alcohol from a carboxylic acid ester by a simple process and without the use of an entrainer is provided, wherein a liquid, which contains a carboxylic acid ester and in which at least a part of the components thereof is comprised of aside stream taken out from a first distillation tower operated in the total reflux condition, is fed into a hydrolysis reactor filled with an acid catalyst to obtain a reaction product liquid, comprised essentially of carboxylic acid, alcohol, water and carboxylic acid ester, this reaction product liquid is fed into the abovementioned first distillation tower, a bottom liquid, comprised essentially of carboxylic acid, alcohol, and water, is taken out from the bottom of this distillation tower, this bottom liquid is separated in a second distillation tower into a top distillate, having alcohol as the principal component, and a bottom liquid, comprised of carboxylic acid and water, this bottom liquid is separated in a third distillation tower into a top distillate, comprised of carboxylic acid and water, and a bottom liquid, comprised of carboxylic acid, and this top distillate is circulated beck to the tower top of the first distillation tower and water is added to this tower top. Or, a liquid, which contains a carboxylic acid ester is fed into a first distillation tower, operated in the total reflux condition, a side stream form the first distillation tower is fed into a hydrolysis reactor filled with acid catalyst, the reaction product liquid, comprised essentially of carboxylic acid, alcohol, water, and carboxylic acid ester, is fed into the abovementioned first distillation tower, and thereafter distillation is performed in the same manner as described above.

Having generally described this invention, a further understanding can be obtained by reference to certain specific examples, which are provided herein for purposes of illustration only, and are not intended to be limiting unless otherwise specified.

EXAMPLES

Example 1

Acetic acid and methanol were produced from methyl acetate in accordance with the flow illustrated in FIG. 1. The side stream taken out from the fourth stage from the tower top of the first distillation tower was added to a methylacetate-containing liquid, with a methyl acetate content of 94.4 wt % and a water content of 5.6 wt %, from the methyl acetate feeding line to provide a methyl-acetate-containing mixed liquid, comprised of 17.3 wt. % water, 74.1 wt % methyl acetate, 7.6 wt % methanol, and 1.0 wt % acetic acid, and this mixed liquid was fed into a stainless-steel hydrolysis reactor with an 2800 mm inner diameter and a 3600 mm length, which was filled with a porous acidic ion exchange resin (PK 228LH, made by Mitsubishi Chemical Co. Ltd.), and a reaction product liquid, comprised of 13.8 wt % water, 59.8 wt % methyl acetate, 13.8 wt % methanol, and 12.6 wt % acetic acid, was obtained. This reaction product liquid was fed into the fourth stage from the tower top of the stainlesssteel first distillation tower, which is comprised of 35 stages of perforated plates and has an inner diameter of 3000 mm, and was subject to extractive distillation. Upon performing atmospheric distillation in the total reflux condition, a bottom liquid, comprised of 41.3 wt % acetic acid, 21.2 wt % methanol, and 37.5 wt % water, was obtained. As has been mentioned above, the side stream was taken out from the fourth stage from the tower top of the first distillation tower, mixed with the mixed liquid of methyl acetate and water fed from the methyl acetate feeding line, and fed to the hydrolysis reactor. The bottom liquid of the first distillation tower was fed to the 45th stage of the second distillation tower, which is comprised of 65 stages of perforated plans and has an inner diameter of 1500 mm, and was separated at a reflux ratio of 1.45 into a top distillate, comprised of 99.95 wt % methanol, and a bottom liquid, comprised of acetic acid and water. The top distillate was used as product methanol.

The bottom liquid of the second distillation tower was an aqueous solution with an acetic acid concentration of 43.1 wt %, and this was fed into the 24th stage from the tower top of the stainless-steel third distillation tower, which is comprised of 35 stages of perforated plates and has an inner diameter of 3600 mm. Upon performing atmospheric distillation with the reflux ratio maintained at 1.44, a 7.4 wt % aqueous acetic acid solution was obtained from the tower top, and a 99.95 wt % acetic acid was obtained from the bottom. The acetic acid was taken out from near the bottom as a side stream and used as product. The top distillate was circulated back along with added water and used as solvent in the above-described first distillation tower. The quantity of heat required for separation, as converted into 4 kg/cm$^2$G steam. was 4 kg per 1 kg of raw material methyl acetate. With regard to the number of distillation towers used, this example was carried out in accordance with a flow that is simpler than the comparative example described below, and the operation of third distillation tower 7 was extremely easy.

Example 2

Acetic acid and methanol were produced from methyl acetate in accordance with the flow shown in FIG. 2. A liquid, comprised of 1.9 wt % water, 31.4 wt % methyl acetate, and 66.7 wt % methanol, was fed into the 19th stage from the tower top of the stainless-steel first distillation tower, which is comprised of 45 stages of perforated plates and has an inner diameter of 3200 mm, and was subject to extractive distillation. Upon performing atmospheric distillation in the total reflux condition, a bottom liquid, comprised of 20.5 wt % acetic acid, 58.0 wt % methanol, and 21.5 wt % water, was obtained. The bottom liquid of the first distillation tower was fed to the 50th stage of the second distillation tower, which is comprised of 65 stages of perforated plates and has an inner diameter of 2800 mm, and was separated at a reflux ratio of 1.45 into a top distillate, comprised of 99.95 wt % methanol, and a bottom liquid, comprised of acetic acid and water. The top distillate was used es product methanol.

The bottom liquid of the second distillation tower was an aqueous solution with an acetic acid concentration of 41.4 wt %, and this was fed into the 28th stage from the tower top of the stainless-steel third distillation tower, which is comprised of 70 stages of perforated trays and has an inner diameter of 3600 mm. Upon performing atmospheric distillation with the reflux ratio maintained at 1.44, a 7. 1 wt % aqueous acetic acid solution was obtained from the tower top, and a 99.95 wt % acetic acid was obtained from the bottom. The acetic acid was taken out from near the bottom as a side stream and used as product. The top distillate was circulated back along with added water and used as solvent in the above-described first distillation tower.

A side stream was taken out from the 4th stage from the tower top of the first distillation tower, supplied to the same hydrolysis reactor as the first example to obtain a reaction product liquid, comprised of 17.5 wt % water, 71.3 wt % methyl acetate, 9.8 wt % methanol, and 1.4 wt % acetic acid, and this reaction product liquid was fed into the 5th stage from the tower top of the first distillation tower 10. The quantity of heat required for separation, as converted into 4 kg/cm$^2$G steam, was 5 kg per 4 1kg of raw material methyl acetate. The number of distillation towers used was the same as that of the first example and acetic acid and methanol were obtained in accordance with a simple flow. Also, the operation of third distillation tower 15 was extremely easy.

Comparative Example

Acetic acid and methanol were produced from methyl acetate in accordance with the flow shown in FIG. 3. A saponification mother liquor, comprised of 36 wt % methyl acetate and 64 wt % methanol, was fed into the 6th stage from the top of the A distillation tower, comprised of 36 stages, and was separated at a reflux ratio of 1.0 into a top distillate, comprised of 78 wt % methyl acetate and 22 wt % methanol, and a bottom liquid, comprised of methanol. The top distillate was fed along with the top distillate, comprised of 67 wt % methyl acetate, 30 wt % methanol, and 3 wt % water, from the B distillation tower into the extractive distillation tower. The extractive distillation tower is a distillation tower of 30 stages, and the distillate from the A distillation tower was fed to the 16th stage and the distillate from the B distillation tower was-ed to the 19th stage. Water was added from the tower top of the extractive distillation tower and extractive distillation was performed at a reflux ratio of 0.35.

The bottom liquid of the extractive distillation tower was an aqueous solution of approximately 25 wt % methanol, and this, along with the abovementioned bottom liquid of the A distillation tower, was fed into the 36th stage of the 56th stage C distillation tower and separated into a methanol distillate and a bottom liquid, containing sodium acetate, etc., at a reflux ratio of 1.4. The top distillate of the extractive distillation tower was a liquid having 41 wt % methyl acetate and 59 wt % water as the main components, and this liquid was fed into a stainless-steel hydrolysis reactor, with an inner diameter of 2400 mm and length of 3600 mm and filled with the same ion exchange resin as the first example, and a reaction product liquid, which was comprised of 17 wt % acetic acid, 9 wt % methanol, 54 wt % water, and 20 wt % methyl acetate, was obtained. This reaction product liquid was supplied to the B distillation tower and separated into a top distillate, comprised of 67 wt % methyl acetate, 30 wt % methomethanol, and 3 wt % water, and a bottom liquid, comprised of a 24 wt % aqueous solution of acetic acid. The top distillate was the abovementioned return distillate and this distillate was fed to the extractive distillation tower.

The bottom liquid, comprised of acetic acid and water, of the B distillation tower was fed to the top of the 45-stage extraction tower, and butyl acetate of an amount that was 1.6 times the amount of the bottom liquid fed was fed from the lower pert of the extraction tower to extract acetic acid. The extract liquid from the tower top of the extraction tower was comprised of 13 wt % acetic acid, 79 wt % butyl acetate, and 8 wt % water, and this extract liquid was fed into the 20th stage of a 65-stage azeotropic distillation tower using butyl acetate as the entrainer, and acetic acid was recovered at a reflux ratio of 0.35 from the lower part of the distillation tower. The top distillate of the azeotropic distillation tower was comprised of water and solvent, this top distillate was separated using a liquid separator, and the solvent was circulated back and used in the extraction tower. With this production method, the required quantity of heat, as converted into 4kg/cm$^2$G steam, was 6 kg per 4 1kg of raw material methyl acetate, the number of distillation towers used was large, and the operation flow was complex. Also, the azeotropic distillation tower had to be operated so that water and butyl acetate will not become mixed in the bottom liquid of this distillation tower, and a large amount of labor was required for this procedure. Also, the amount of water used as extraction water was approximately twice that of the examples described above and amount of waste water was approximately 100 times that of the examples described above.

This application is based on Japanese patent application 169331/1999, filed Jun. 16, 1999, the entire contents of which are hereby incorporated by reference.

Obviously, numerous modifications and variations of the present invention are possible in light of the above teachings. It is therefore to be understood that within the scope of the appended claims, the invention may be practiced otherwise than as specifically described herein.

What is claimed is:

1. A method of producing carboxylic acid and alcohol, comprising:

hydrolysing a liquid in a hydrolysis reactor, said hydrolysis reactor comprising an acid catalyst, and said liquid comprising: (1) a carboxylic acid ester; and (2) at least a portion of a side stream taken from a first distillation tower operated in a total reflux condition, to obtain a reaction product liquid comprising a carboxylic acid, an alcohol, water and a carboxylic acid ester;

supplying said reaction product liquid to said first distillation tower and removing a first bottom liquid therefrom, said first bottom liquid comprising a carboxylic acid, an alcohol and water;

supplying said first bottom liquid to a second distillation tower and separating said first bottom liquid into a first top distillate comprising an alcohol, and a second bottom liquid comprising a carboxylic acid and water;

supplying said second bottom liquid to a third distillation tower and separating said second bottom liquid into a second top distillate comprising a carboxylic acid and water, and a third bottom liquid comprising a carboxylic acid;

circulating said second top distillate back to a tower top of said first distillation tower, and adding water to said tower top.

2. The method according to claim 1, wherein the carboxylic acid is selected from the group consisting of propionic acid, acetic acid, butyric acid, valeric acid, caproic acid and lactic acid.

3. The method according to claim 1, wherein the alcohol is selected from the group consisting of methanol, ethanol, propanol and butanol.

4. The method according to claim 1, wherein the carboxylic acid ester is acetic acid ester.

5. The method according to claim 4, wherein the acetic acid ester is methylacetate or ethyl acetate.

6. The method according to claim 1, wherein the acid catalyst is a solid acid catalyst.

7. The method according to claim 6, wherein the solid acid catalyst comprises an ion exchange resin.

8. The method according to claim 1, wherein the first distillation tower is a plate tower comprising 25 to 60 stages.

9. The method according to claim 8, wherein the plate tower comprises 30 to 40 stages.

10. The method according to claim 1, wherein a ratio of water to carboxylic acid in the first bottom liquid is in the range of 1:1 to 1:4.

11. A method of producing carboxylic acid and alcohol, comprising:

supplying a liquid to a first distillation tower, said liquid comprising a carboxylic acid ester, and said first distillation tower being operated in a total reflux condition, to obtain a side stream;

supplying said side stream to a hydrolysis reactor comprising an acid catalyst to obtain a reaction product liquid comprising a carboxylic acid, an alcohol, water and a carboxylic acid ester;

supplying said reaction product liquid to said first distillation tower and removing a first bottom liquid therefrom, said first bottom liquid comprising a carboxylic acid, an alcohol and water;

supplying said first bottom liquid to a second distillation tower and separating said first bottom liquid into a first top distillate comprising an alcohol, and a second bottom liquid comprising a carboxylic acid and water;

supplying said second bottom liquid to a third distillation tower and separating said second bottom liquid into a second top distillate comprising a carboxylic acid and water, and a third bottom liquid comprising a carboxylic acid;

circulating said second top distillate back to a tower top of said first distillation tower, and adding water to said tower top.

12. The method according to claim 11, wherein the carboxylic acid is selected from the group consisting of propionic acid, acetic acid, butyric acid, valeric acid, caproic acid, and lactic acid.

13. The method according to claim 11, wherein the alcohol is selected from the group consisting of methanol, ethanol, propanol and butanol.

14. The method according to claim 11, wherein the carboxylic acid ester is acetic acid ester.

15. The method according to claim 14, wherein the acetic acid ester is methylacetate or ethyl acetate.

16. The method according to claim 11, wherein the acid catalyst is a solid acid catalyst.

17. The method according to claim 16, wherein the solid acid catalyst comprises an ion exchange resin.

18. The method according to claim 11, wherein the first distillation tower is a plate tower comprising 30 to 70 stages.

19. The method according to claim 11, wherein the second bottom liquid is an aqueous solution comprising carboxylic acid in a concentration of approximately 20 to 50 wt. %.

* * * * *

UNITED STATES PATENT AND TRADEMARK OFFICE
CERTIFICATE OF CORRECTION

PATENT NO. : 6,462,231 B1  Page 1 of 1
DATED : October 8, 2002
INVENTOR(S) : Yanagawa et al.

It is certified that error appears in the above-identified patent and that said Letters Patent is hereby corrected as shown below:

<u>Column 4,</u>
Line 55, "as. the" should read -- as the --.

<u>Column 5,</u>
Line 16, "carboxylic-acidester-containing" should read -- carboxylic-acid-ester-containing --.

<u>Column 7,</u>
Line 49, "catalyst. and" should read -- catalyst, and --.

<u>Column 8,</u>
Line 47, "water. and" should read -- water and --.

<u>Column 10,</u>
Line 8, "stainlesssteel" should read -- stainless-steel --;
Line 40, "steam. was" should read -- steam was --.

<u>Column 11,</u>
Line 11, "4 1kg" should read -- 1 kg --;
Line 41, "was-ed" should read -- was fed --.

<u>Column 12,</u>
Line 15, "4 1kg" should read -- 1 kg --.

Signed and Sealed this

Sixth Day of May, 2003

JAMES E. ROGAN
*Director of the United States Patent and Trademark Office*